United States Patent [19]

Edwards

[11] Patent Number: 4,739,757
[45] Date of Patent: Apr. 26, 1988

[54] OXYGEN TUBE RETAINING HEADBAND

[76] Inventor: Anna M. Edwards, 189 Meyer St., Edwardsville, Pa. 18794

[21] Appl. No.: 929,827

[22] Filed: Nov. 13, 1986

[51] Int. Cl.⁴ .............................................. A61M 51/08
[52] U.S. Cl. ...................... 128/207.18; 128/DIG. 26; 604/174
[58] Field of Search ...................... 128/207.17, 207.18, 128/207.11, 204.11, DIG. 26, 207.13; 604/179, 174

[56] References Cited

U.S. PATENT DOCUMENTS

| | | | |
|---|---|---|---|
| 1,443,820 | 1/1923 | Hudson | 128/207.18 |
| 2,245,969 | 6/1941 | Francisco et al. | 128/207.18 |
| 2,259,817 | 10/1941 | Hawkins | 128/207.18 |
| 2,292,568 | 8/1942 | Kanter et al. | 128/204.11 |
| 2,353,643 | 7/1944 | Bulbulian | 128/207.11 |
| 3,648,703 | 3/1972 | Manker | 128/207.18 |
| 3,972,321 | 8/1976 | Proctor | 128/207.8 |
| 4,018,221 | 4/1977 | Rennie | 128/207.18 |
| 4,331,143 | 5/1982 | Foster | 128/DIG. 26 |
| 4,373,523 | 2/1983 | Treutelaav | 128/207.18 |
| 4,406,283 | 9/1983 | Biv | 128/207.18 |
| 4,480,639 | 11/1984 | Peterson et al. | 128/207.18 |
| 4,485,822 | 12/1984 | O'Connor et al. | 128/DIG. 26 |

Primary Examiner—Edward M. Coven
Assistant Examiner—K. M. Reichle
Attorney, Agent, or Firm—David A. Tamburra

[57] ABSTRACT

A headband for supporting a nasal oxygen administering tube on the head of a patient. The headband includes a pair of adjustable straps extending over the top and around the back of a patient's head. The ends of one of the straps are foldable back upon themselves to form loops positioned in front of the patient's ears for supporting a tube without irritating the ears and face.

5 Claims, 1 Drawing Sheet

OXYGEN TUBE RETAINING HEADBAND

BACKGROUND AND SUMMARY OF THE INVENTION

This invention relates generally to head mounting devices for oxygen administering tubes, and more particularly to a novel headband which securely and comfortably supports the oxygen tube on a patient's head.

Oxygen tube supporting devices of various types and design have been proposed in the past. Typical of those are shown in U.S. Pat. Nos. 4,480,639, 4,406,283, 4,018,221, 3,972,321, and 2,245,969. None however, satisfactorily supports the tube without irritating the patient's head or face in some fashion.

Accordingly, the primary object of this invention is to provide a novel headband of simple construction which securely and comfortably supports an oxygen tube on a patient's head. Consequently, for long term oxygen users, the novel headband eliminates blistering of the top and back of the ears and irritation of the nose.

Another object of the invention is to provide a novel headband comprising a pair of flexible fabric straps extending over the top and around the back of a patient's head, with the ends of one the straps being foldable upon themselves to form support loops through which an oxygen tube may pass.

Still another object of the invention is to provide a headband as above, wherein the straps are adjustably connected together to conform to any size head.

A further object of this invention is to provide a headband as above, wherein the straps are substantially perpendicular to each other to securely mount the headband and oxygen tube on the head.

Other objects and advantages will become evident from reading the following detailed description of the invention with reference to the accompanying drawings wherein like numerals indicate like elements.

Figure 1:
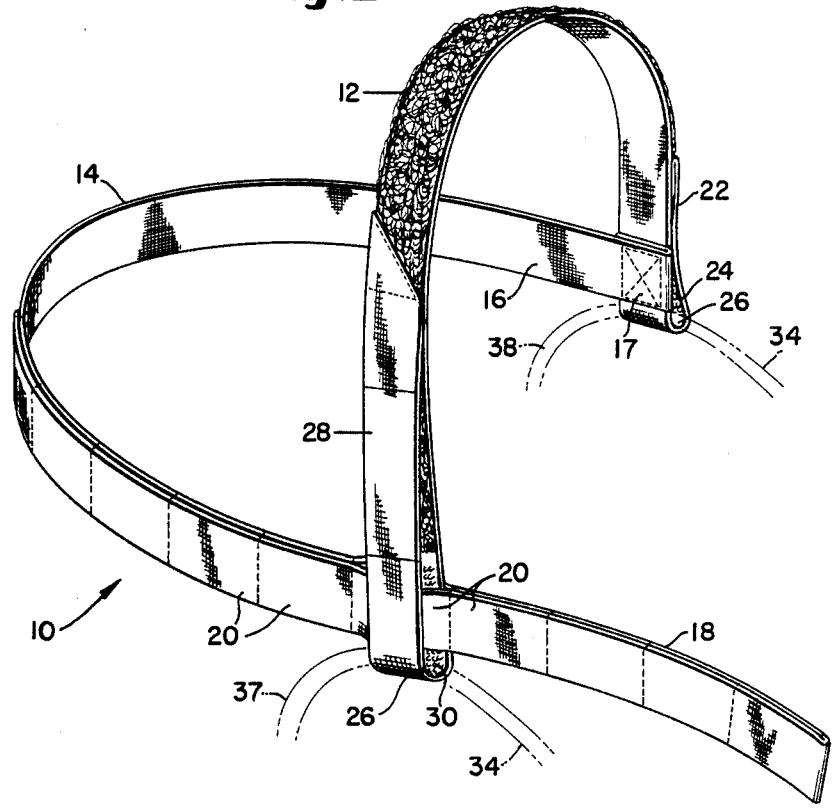
FIG. 1 is a generally perspective view of the novel oxygen tube supporting headband of the invention.

Referring now to the drawings, the novel headband 10 of the invention fits on a patient's head 11 and comprises a pair of flexible, soft fabric straps 12 and 14 which extend, respectively, over the top and around the back of the patient's head 11. Straps 12 and 14 are substantially perpendicular to each other and fit securely on head 11.

One end 16 of strap 14 is sewn at 17 to strap 12 while the other end 18 is formed with a plurality of stitched pockets 20. One end 22 of strap 12 is provided on its outside face with a Velcro connector 24 and is foldable back upon itself to form loop 26. The other end 28 of strap 12 passes through a selected one of pockets 20 to provide size adjustment for strap 14 around the back of head 11. End 28 on its outside face is also provided with a Velcro connector 30 and is foldable back upon itself to form a tube holding loop similar to loop 26.

Figure 2:
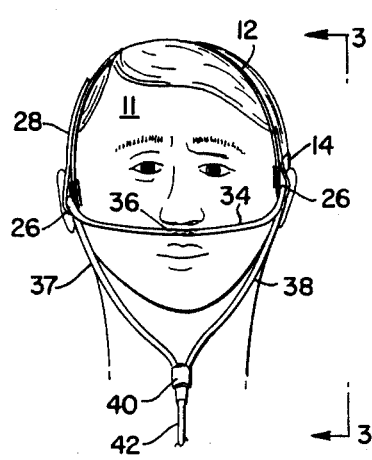
FIG. 2 is a front elevation view showing the novel headband supporting an oxygen tube on a patient's head.
Figure 3:
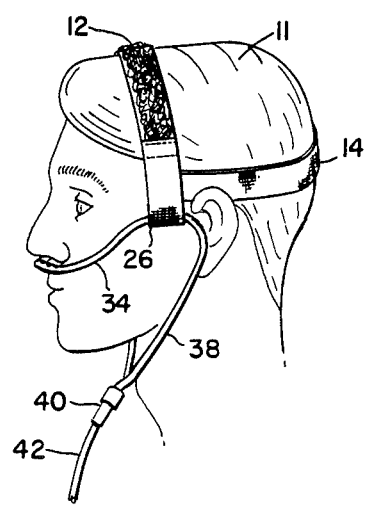
FIG. 3 is a side elevation taken along line 3—3 of FIG. 2.

FIGS. 2 and 3 illustrate how headband 10 fits on to a patient's head 11. End 28 is placed through a selected one of pockets 20 and pull downwardly so that straps 12 and 14 properly and securely fit on head 11. The ends 22 and 28 are folded back upon themselves to form loops 26 which are normally positioned in front of the patient's ears. Once the headband has been properly sized, the extra material on ends 18 and 28 may be cut off.

An oxygen tube 34, which has openings 36 adjacent the patient's nose, has its ends 37 and 38 extending rearwardly through loops 26 and down to a common fitting 40 which receives oxygen from feeder line 42.

From the description hereinabove, it is clear that headband 10 very comfortably and securely adjusts to and mounts on the patient's head 11. The loops 26 support oxygen tube 34 and prevent the tube from irritating the patient's ears and face.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A headband for holding an oxygen breathing tube on the head of a patient, the tube being of the type which includes first and second opposite ends, means for connecting said ends to a source of oxygen and fluid communication means between said ends for providing oxygen to the patient, said headband comprising first strap means adapted to extend over the top of said head from side to side, second strap means adapted to extend around the back of said head, said first and second strap means each having first and second opposite ends and each of said respective opposite ends being connected together at points adapted to lie on opposite sides of the head, respectively, each end of one of said strap means extending beyond said point of connection and being foldable back upon itself to form loop means suitable to receive the first and second ends of the tube, respectively, therethrough to hold it in place, and means for holding said ends of said one strap means folded back.

2. The headband of claim 1, comprising means adjustably connecting said first and second strap means together so that said headband may be adjusted for size.

3. The headband of claim 1, wherein the ends of said first strap means are foldable upon themselves to form tube-holding loop means.

4. The headband on claim 1, said first and second strap means being arranged substantially perpendicular to each other.

5. The headband of claim 1, comprising means adjustably connecting said first and second strap means together so that said headband may be adjusted for size, and the ends of said first strap means being foldable upon themselves to form said tube holding loop means.

* * * * *